US012778383B2

(12) United States Patent
Harrah et al.

(10) Patent No.: US 12,778,383 B2
(45) Date of Patent: Nov. 3, 2026

(54) ENDOSCOPY SYSTEMS AND RELATED METHODS

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Derrick Lenz, Pompton Plains, NJ (US); Arpita Banerjee, Bangalore (IN); Sandesh Gavade, Bangalore (IN); Pavan Misra, Bangalore (IN); Abhijit Takale, Pune (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 519 days.

(21) Appl. No.: 17/809,593

(22) Filed: Jun. 29, 2022

(65) Prior Publication Data

US 2022/0400941 A1 Dec. 22, 2022

Related U.S. Application Data

(63) Continuation of application No. 15/416,292, filed on Jan. 26, 2017, now Pat. No. 11,406,253.

(Continued)

(51) Int. Cl.

*A61B 1/00* (2006.01)
*A61B 1/005* (2006.01)

(Continued)

(52) U.S. Cl.

CPC ...... *A61B 1/00042* (2022.02); *A61B 1/00039* (2013.01); *A61B 1/00052* (2013.01);

(Continued)

(58) Field of Classification Search

CPC . A61B 1/0051; A61B 1/0052; A61B 1/00066; A61B 1/00133; A61B 34/30

See application file for complete search history.

(56) References Cited

U.S. PATENT DOCUMENTS 6,682,426 B2 1/2004 Goto et al.
9,044,138 B2 6/2015 Sjostrom et al.

(Continued)

OTHER PUBLICATIONS

International Search Report and Written Opinion for International Application No. PCT/US2017/014950, mailed Mar. 29, 2017 (12 pages).

*Primary Examiner* — Alexandra L Newton

(74) *Attorney, Agent, or Firm* — Bookoff McAndrews PLLC

(57) ABSTRACT

According to one aspect, an endoscope system may include a shaft having a proximal end and a distal portion configured for insertion into a subject. The distal portion may have a distal end. The shaft may also include a lumen extending between the proximal end and the distal end. The lumen may be configured to receive an instrument extendable through the lumen of the shaft. The endoscope system may also include a visualization system coupled to the shaft for visualizing a region distal to the distal end of the shaft. The endoscope system may also include a handle coupled to the proximal end of the shaft. The handle may be configured for gripping by a user. The handle may include a shaft control system for controlling operation of the shaft. The handle may also include an instrument control system for controlling operation of an instrument extendable through the shaft.

20 Claims, 8 Drawing Sheets

Related U.S. Application Data

(60) Provisional application No. 62/288,875, filed on Jan. 29, 2016.

(51) Int. Cl.

| | |
|---|---|
| ***A61B 1/018*** | (2006.01) |
| ***A61B 1/04*** | (2006.01) |
| ***A61B 1/06*** | (2006.01) |
| ***A61B 1/307*** | (2006.01) |
| ***A61B 17/00*** | (2006.01) |
| ***G02B 23/24*** | (2006.01) |

(52) U.S. Cl.

CPC ...... *A61B 1/00066* (2013.01); *A61B 1/00133* (2013.01); *A61B 1/00149* (2013.01); *A61B 1/0016* (2013.01); *A61B 1/00165* (2013.01); *A61B 1/00188* (2013.01); *A61B 1/0051* (2013.01); *A61B 1/04* (2013.01); *A61B 1/0676* (2013.01); *A61B 1/307* (2013.01); *G02B 23/2476* (2013.01); *A61B 1/0052* (2013.01); *A61B 1/018* (2013.01); *A61B 2017/00389* (2013.01)

(56) References Cited

U.S. PATENT DOCUMENTS

| | | | |
|---|---|---|---|
| 9,089,352 | B2 | 7/2015 | Jeong |
| 2003/0176778 | A1 | 9/2003 | Messing et al. |
| 2004/0133075 | A1 | 7/2004 | Motoki et al. |
| 2005/0119527 | A1 | 6/2005 | Banik et al. |
| 2005/0222499 | A1 | 10/2005 | Banik et al. |
| 2005/0267327 | A1 | 12/2005 | Izuka et al. |
| 2007/0015968 | A1 | 1/2007 | Shelnutt |
| 2008/0262311 | A1 | 10/2008 | Itou et al. |
| 2009/0149709 | A1 | 6/2009 | Koitabashi |
| 2011/0245603 | A1 | 10/2011 | Brannon |
| 2012/0150155 | A1 | 6/2012 | Kappel et al. |
| 2012/0209065 | A1 | 8/2012 | Hosaka et al. |
| 2014/0316203 | A1 | 10/2014 | Carroux et al. |
| 2015/0031953 | A1 | 1/2015 | Atarot et al. |
| 2015/0112141 | A1 | 4/2015 | Oginski et al. |
| 2015/0216396 | A1 | 8/2015 | Banik et al. |
| 2015/0320298 | A1* | 11/2015 | Missov .................. A61B 90/50 248/51 |
| 2016/0213239 | A1 | 7/2016 | Fujii |
| 2017/0095299 | A1* | 4/2017 | Hendrick ......... A61B 17/00234 |
| 2017/0172389 | A1* | 6/2017 | Fujisaki ............. A61B 1/00142 |
| 2018/0279992 | A1* | 10/2018 | Frankel ................ A61G 13/101 |

* cited by examiner

ENDOSCOPY SYSTEMS AND RELATED METHODS

CROSS-REFERENCE TO RELATED APPLICATIONS

This application is a continuation of and claims the benefit of priority to U.S. Non-provisional patent application Ser. No. 15/416,292 filed on Jan. 26, 2017, which claims the benefit of priority of U.S. Provisional Application No. 62/288,875, filed Jan. 29, 2016, the entirety of which are incorporated by reference into this application.

TECHNICAL FIELD

Various aspects of the present disclosure relate generally to endoscopy systems and related methods. More specifically, the present disclosure relates to control features of endoscopy systems and related methods.

BACKGROUND

The field of endoscopy covers systems and methods a user may employ to examine and/or treat a subject with, e.g., the assistance of an endoscope or other suitable introduction sheaths or devices. An endoscope (or other suitable introduction device) may provide for viewing of, for example, the interior of a hollow organ or cavity in the subject's body. Ureteroscopy and pyeloscopy are subsets of endoscopy. Ureteroscopy may include procedures in which an endoscope (such as, e.g., a ureteroscope) may be passed through the subject's urethra and bladder, and directly into the subject's ureter. The endoscope may be further inserted into the subject's kidney for pyeloscopic procedures. These procedures may be useful in the diagnosis and the treatment of disorders of the subject's urinary tract, such as the presence of kidney stones that may block urinary tract ducts. Many approaches are available for treating such stones, including, for example, laser treatment and subsequent removal of the stones from the body. Enhancing control of the endoscope during performance of such procedures may lead to improved outcomes.

Moreover, conventional approaches to endoscopic procedures may require steps to be performed by more than one user. For example, in some instances, one user may be tasked with controlling the endoscope, another user may be tasked with positioning an instrument inserted through the endoscope, and yet another user may be tasked with activating the instrument and/or controlling another instrument. Having multiple users may make procedures inefficient and expensive.

SUMMARY

Aspects of the present disclosure relate to, among other things, endoscopy systems and related methods. Each of the aspects disclosed herein may include one or more of the features described in connection with any of the other disclosed aspects.

In one aspect of the present disclosure, an endoscope system may include a shaft. The shaft may include a proximal end and a distal portion configured for insertion into a subject. The distal portion may have a distal end. The shaft may also include a lumen extending between the proximal end and the distal end. The lumen may be configured to receive an instrument extendable through the lumen of the shaft. The endoscope system may also include a visualization system coupled to the shaft for visualizing a region distal to the distal end of the shaft. The endoscope system may also include a handle coupled to the proximal end of the shaft. The handle may be configured for gripping by a user. The handle may include a shaft control system for controlling operation of the shaft. The handle may also include an instrument control system for controlling operation of an instrument extendable through the shaft.

Aspects of the endoscope system may include one or more of the features below. The shaft control system may control one or more actuators for at least one of translating the shaft along a central longitudinal axis of the shaft, rotating the shaft about the central longitudinal axis, and bending the shaft. The visualization system may include a camera assembly at the distal end of the shaft, and the handle may include a visualization control system for controlling at least one of a zoom function and a focusing function of the camera assembly. The instrument control system may control an actuator for translating the instrument along a central longitudinal axis of the instrument. The instrument control system may control delivery of energy by activating the instrument. At least one of the shaft control system and instrument control system may include a button or a switch on the handle, the button or the switch being positioned on the handle for manipulation by the user while the user grips the handle. The handle may be a single unitary handle of the endoscope system. The handle may be configured for gripping by a single hand of the user and for activating the shaft control system and the instrument control system by the single hand.

In another aspect of the present disclosure, an endoscope system may include a shaft. The shaft may include a proximal end, and a distal portion configured for insertion into a subject. The distal portion may have a distal end. The shaft may also include a lumen extending between the proximal end and the distal end. The lumen may be configured to receive an instrument extendable through the lumen of the shaft. The endoscope system may also include a visualization system coupled to the distal end of the shaft for visualizing a region distal to the distal end of the shaft. The endoscope system may also include a handle coupled to the proximal end of the shaft. The handle may be configured for gripping by a user. The handle may be configured to control the shaft and instrument. The endoscope system may also include a base configured for coupling with and supporting the handle. The handle may be movable relative to the base while the base and the handle are coupled.

Aspects of the endoscope system may include one or more of the features below. The handle may include a plurality of buttons or switches positioned on the handle for manipulation by a single hand of the user while the single hand grips the handle. Manipulation of the plurality of buttons or switches may control operation of the shaft and the instrument. At least one of the buttons or switches may be operatively coupled to an actuator for at least one of deflecting the shaft, translating the shaft along a central longitudinal axis of the shaft, and rotating the shaft about the central longitudinal axis. The visualization system may include a camera assembly. At least one of the buttons or switches may be operatively coupled to the visualization system to control at least one of a zoom function and a focusing function of the camera assembly. At least one of the buttons or switches may be operatively coupled to the instrument to control at least one of translation of the instrument along a central longitudinal axis of the instrument via activation of an actuator engaging the instrument, and emission of energy via activation of the instrument. The base may include a joint formed by a first member and a second member. The first member may be pivotable relative to the second member. The handle may be coupled to the first member, such that the handle may be pivotable with the first member relative to the second member. Pivoting of the first member relative to the second member may be facilitated by application of a force on the handle. Upon removal of the force from the handle, the first member may remain fixed in a pivoted state relative to the second member. The base may include a housing having an open end and lateral walls defining a central recess. An end portion of the handle may be coupled to the proximal end of the shaft. The central recess may be configured to receive the end portion of the handle via the open end.

In another aspect of the present disclosure, a method for performing a procedure on a subject with an endoscope system may include gripping a handle coupled to a proximal end of shaft. The method may also include positioning a distal end of a distal portion of the shaft at a target area in the subject. The method may also include visualizing the target area with a visualization system at the distal end of the shaft. The method may also include positioning a distal end of a distal portion of an instrument at the target area, the instrument extending through a lumen of the shaft. The method may also include controlling operation of the shaft and the instrument using a single hand gripping the handle.

Aspects of the method for performing the procedure may include one or more of the features below. Controlling operation of the shaft and the instrument may include manipulating buttons or switches on the handle. The buttons or switches may be operatively coupled to the shaft and the instrument. The buttons may be accessible to the user while the user is gripping the handle. Controlling operation of the instrument may include manipulating a button or a switch on the handle to move the instrument translationally along a central longitudinal axis of the instrument. Controlling operation of the instrument may include manipulating a button or a switch on the handle to activate the instrument for delivering laser energy to the target area.

It may be understood that both the foregoing general description and the following detailed description are exemplary and explanatory only and are not restrictive of the features claimed.

As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn generally to endoscopy systems and related methods, and more specifically to control features of endoscopy systems and related methods. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing an instrument into a subject. By contrast, the term "proximal" refers to a portion closest to the user when placing the instrument into the subject. Though the following description refers to "endoscope" or "endoscopy," the principles/aspects described herein may be used with any suitable introduction sheath or device, even if such sheath or device fails to include one or more features typically associated with "endoscopes."

Figure 1:
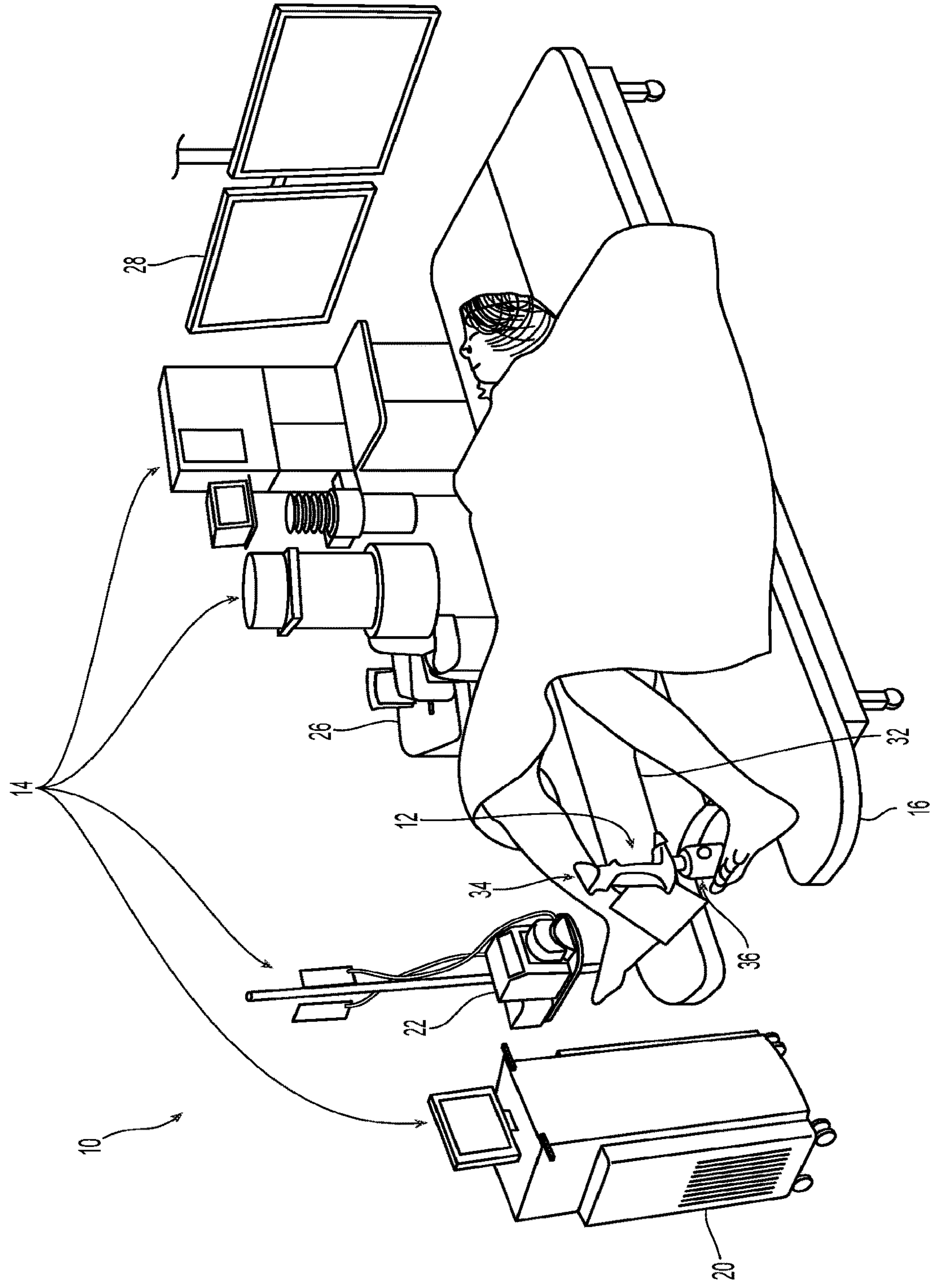
FIG. 1 is a perspective view of an endoscopy system, in accordance with aspects of the present disclosure.
Figure 2:
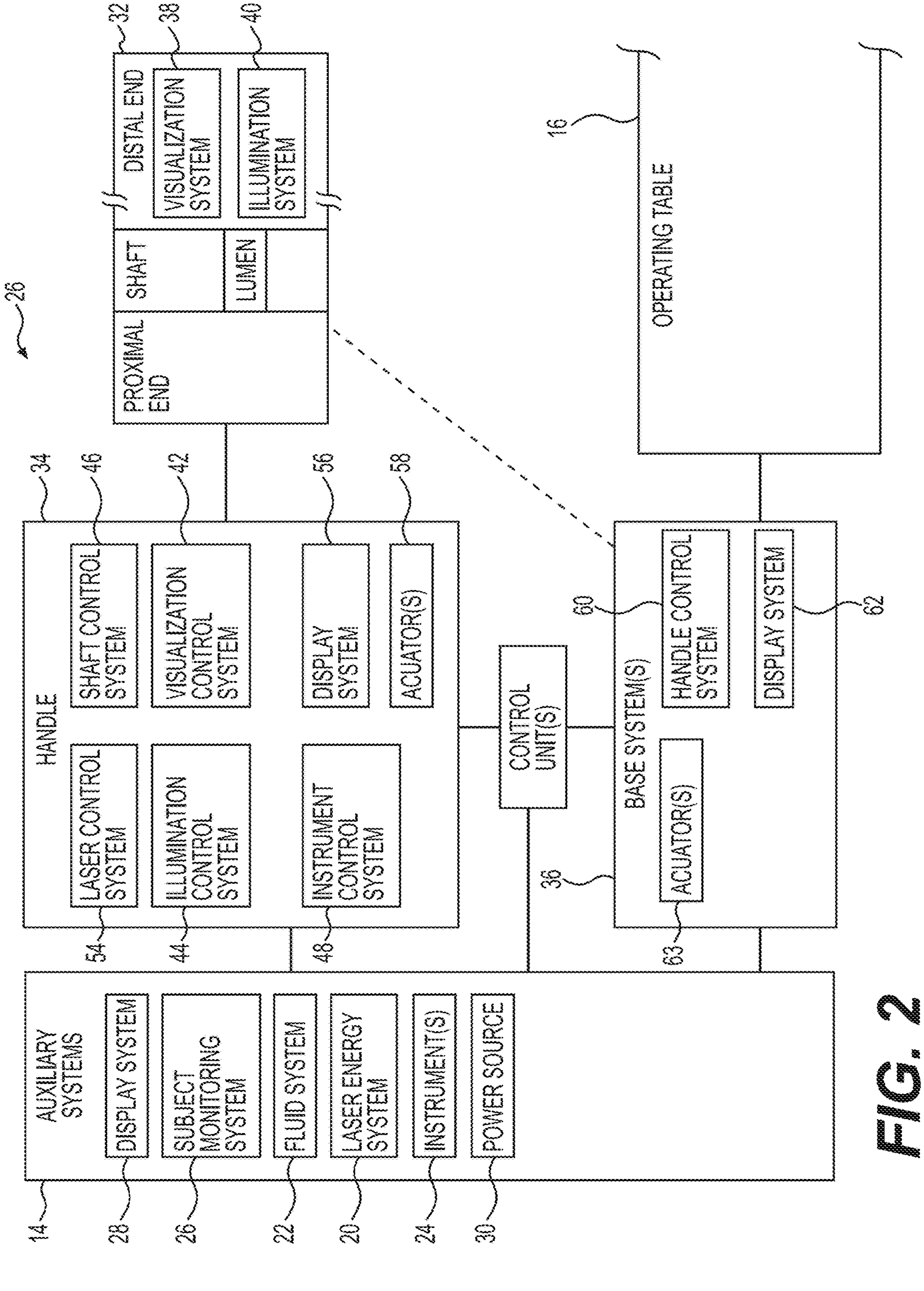
FIG. 2 is a schematic depiction of an endoscopy system, in accordance with aspects of the present disclosure.

FIGS. 1 and 2 show aspects of an exemplary endoscopy system 10. Endoscopy system 10 may include an endoscope system 12, one or more auxiliary systems 14 that may be operatively coupled to endoscope system 12, an operating table 16 for supporting a subject, and one or more control units 18 (FIG. 2) operatively coupled to endoscope system 12 and/or auxiliary system(s) 14. Endoscope system 12, either alone or with the assistance of control unit(s) 18 and auxiliary system(s) 14, may be used to examine and/or treat the subject. Auxiliary system(s) 14 may include, for example, a laser energy system 20, a fluid system 22, one or more instruments 24, a subject monitoring system 26, a display system 28, and/or a power source 30 (FIG. 2).

Endoscope system 12 may include a shaft 32 and a handle 34. In some but not all examples, endoscope system 12 may include a base 36. Shaft 32 may be inserted into the subject's body, and may be guided to a target area therein. Handle 34 and base 36 may be configured to remain outside of the subject's body, such that handle 34 and/or base 36 may be manipulated by a user to insert shaft 32 into, and navigate shaft 32 through, the subject's body. Base 36 may support the weight of handle 34, and to some extent, the weight of at least a portion of shaft 32. Because the user is freed from that burden, the user may experience less fatigue. Moreover, the user may be able to use one or both of his or her hands to perform other tasks without dropping or otherwise displacing handle 34 and shaft 32. Additionally or alternatively, the user may be able to use his or her thumbs and/or fingers to perform other tasks, even while gripping handle 34, without dropping or otherwise displacing handle 34 and shaft 32. In addition, a single user can perform multiple tasks typically accomplished by multiple users.

At least a portion of shaft 32 may be flexible, in that the portion may bend, twist, elongate, compress, or otherwise deform during use. For example, at least the distal portion of shaft 32 may be flexible. One or more steering cables (not shown) may extend through at least a portion of shaft 32. For example, the steering cable(s) may extend through one or more lumens within shaft 32. By pushing and/or pulling the steering cable(s) either individually or in combination, shaft 32 may be bent, tilted, or otherwise deflected.

Shaft 32 may include one or more lumens. The lumen(s) may receive one or more fluids, instrument(s) 24, steering cables, and/or any other suitable components or materials. The lumen(s) may extend between the proximal and distal ends of shaft 32. The lumen(s) may terminate at the distal end of shaft 32 at one or more openings (not shown). The fluid(s) and/or other materials may be emitted from the lumen(s), or suctioned into the lumen(s), via the opening(s) at the distal end of shaft 32. Additionally or alternatively, the instrument(s) 24 may be extended out of the lumen(s) and retracted into the lumen(s) via the opening(s).

Shaft 32 may include a visualization system 38 (FIG. 2). Visualization system 38 may be mounted within the distal end of shaft 32. Visualization system 38 may include a camera assembly (not shown), such as a digital camera having a field of view covering an area distal to the distal end of shaft 32. One or more cables/wires (not shown) may extend proximally from the digital camera to handle 34, base 36, and/or control unit(s) 18 to, for example, supply the digital camera with power, send control signals to the digital camera, and receive image data from the digital camera. Alternatively, visualization system 38 may include a fiber optic assembly (not shown) extending proximally from the distal end of shaft 32 for delivering light (forming an image) to handle 34, base 36, and/or control unit(s) 18.

Shaft 32 may include an illumination system 40 (FIG. 2). Illumination system 40 may include one or more illumination devices including, for example, one or more light-emitting diode assemblies (not shown), light-transmitting fiber optic assemblies (not shown), and/or any other suitable devices for emitting light distally from the distal end of shaft 32. The illumination device(s) may be mounted within the distal end of shaft 32, and may be positioned proximate the camera assembly to illuminate the camera assembly's field of view. One or more cables/wires (not shown) and/or optical fibers (not shown) may extend proximally from the illumination device(s) to handle 34, base 36, and/or control unit(s) 18 to, for example, supply the illumination device(s) with power, and send control signals to the illumination device(s).

Handle 34 may be operatively coupled to the proximal end of shaft 32. Handle 34 may be gripped by the user, and may include one or more control systems configured to be manipulated by the user. The control system(s) may be manipulated while the user grips handle 34 with one or more fingers of the user's gripping hand and/or one or more fingers of the user's free hand.

Handle 34 may include a visualization control system 42 (FIG. 2) for controlling zoom, focus, and/or any other operational parameters of visualization system 38. Handle 34 may further include an illumination control system 44 for controlling activation/deactivation, intensity, and/or any other operational parameters of illumination system 40. Adjusting operational parameters of visualization system 38 and/or illumination system 40 may provide the user with ways to control the quality of image produced by visualization system 38.

Handle 34 may include a shaft control system 46 (FIG. 2) for controlling movement(s) of shaft 32. Shaft 32 may be deflected, which may involve tilting and/or bending (including left-right and up-down movements) one or more portions of shaft 32 by pushing or pulling one or more of the steering cables extending between shaft control system 46 and shaft 32. Additionally or alternatively, shaft 32 may undergo translation. Translation may involve moving shaft 32 proximally and distally. Additionally or alternatively, shaft 32 may rotate about its central longitudinal axis and/or relative to handle 34.

Handle 34 may include an instrument control system 48. Instrument control system 48 may be configured to, for example, move one or more instruments through endoscope system 12. Instrument control system 48 may cause one or more instruments to move distally or proximally so as to extend or retract the instrument(s), respectively, relative to the distal end of shaft 32. Additionally or alternatively, instrument control system 48 may cause one or more instruments to rotate and/or may activate the instruments.

Exemplary instruments include an optical fiber 50 (FIGS. 3A, 5D, 6, and 7) of laser energy system 20, a retrieval basket 52 (FIGS. 4A and 5D), a snare (not shown), an electrode (not shown), and/or any other suitable instrument. Optical fiber 50, retrieval basket system 52, and/or other instruments may extend through the lumen(s) in shaft 32. It is contemplated that the instrument(s) may be inserted into shaft 32 via handle 34 and/or base 36.

Handle 34 may include a laser control system 54 (FIG. 2) for activating laser energy system 20, triggering laser energy system 20 to fire laser energy, and/or sweeping the target area with laser energy. For example, laser control system 54 may include a laser firing control system for triggering the firing of laser energy at a suitable target. The laser energy may be delivered to endoscope system 12 from laser energy system 20 via optical fiber 50. Additionally or alternatively, laser control system 54 may include a laser activation control system for signaling laser energy system 20 prior to firing the laser energy, to prepare laser energy system 20 for firing. Additionally or alternatively, laser control system 54 may a laser sweeping system that may cause a distal tip of shaft 32, and/or a distal tip of a laser energy probe or conductor (e.g., optical fiber 50) extending through shaft 32, to undergo a sweeping movement. An angle of the sweeping movement may be variable. In one example, the sweeping movement may cause the distal tip to swing through anywhere up to a 30 degree arc. The systems for laser sweeping and laser firing may be separately controlled such that one of sweeping and firing may be performed without performing the other. In one example, any suitable mechanical device or actuator, such as one or more of the steering cables of shaft 32, may produce the sweeping movement.

Handle 34 may include a display system 56 (FIG. 2). Display system 56 may include a screen, a monitor, an array of lights, or any other suitable display mechanism. Display system 56 may show, for example, auxiliary systems settings, information on the subject, operational parameters associated with endoscope system 12, and/or any other suitable data. Alternatively, display system 56 may be omitted from handle 34.

Handle 34 may include one or more actuators 58 (FIG. 2) for producing one or more of the above-described shaft and/or instrument movements. For example, actuator(s) 58 may be configured to deflect, translate, and/or rotate shaft 32 when actuator(s) 58 are activated. Additionally or alternatively, actuator(s) 58 may be configured to translate, rotate, or activate one or more instruments, such as optical fiber 50 and retrieval basket system 52, when actuator(s) 58 are activated.

Handle 34 may be operatively coupled to base 36. Base 36 may support handle 34 and/or shaft 32 above the ground and/or on operating table 16, thus freeing the user from carrying the weight of handle 34 and/or shaft 32. Base 36 may include a handle control system 60 to guide, lock, and/or otherwise control movement of handle 34. Additionally or alternatively, base 36 may include a display system 62, such as a screen, a monitor, or any other suitable display mechanism, for showing auxiliary systems settings, information on the subject, operational parameters associated with endoscope system 12, and/or any other suitable data.

While shaft 32 is coupled to handle 34 in FIG. 1, it is contemplated that shaft 32 may be coupled to base 36, such that handle 34 may be operatively coupled to shaft 32 via base 36. Additionally or alternatively, portions of shaft control system 46, laser control system 54, instrument control system 48, and/or actuator(s) 58, may be provided in base 36. Alternatively, base 36 may be omitted, allowing handle 34 and shaft 32 to be utilized free of base 36.

Endoscopy system 10 may include control unit(s) 18 (FIG. 2). Control unit(s) 18 may receive input signals from one or more electronic components of endoscopy system 10, process the input signals, and/or generate output signals for sending to the electronic component(s). Control unit(s) 18 may also include a power control system for controlling the distribution of power from power source 30 to the electronic component(s).

Control unit(s) 18 may be located external to endoscope system 12. Alternatively, one or more portions of control unit(s) 18 may be part of endoscope system 12. For example, one or more portions of control unit(s) 18 may be part of handle 34 and/or base 36. Control unit(s) 18 may communicate with each other and the electronic component(s) via any suitable wired or wireless communications. Control unit(s) 18 may include one or more circuit boards external to endoscope system 12, or contained within handle 34 and/or base 36. It is also contemplated that control unit(s) 18 may include any suitable computing device, such as a tablet computer, configured to communicate with other elements of endoscope system 12 via wired and/or wireless communication means.

It is further contemplated that one or more elements of endoscope system 12 may include a power switch or button for turning the element on or off. For example, at least one of handle 34 and base 36 may include a power switch or button for triggering distribution of power to its electronic components and cutting off that distribution of power. Alternatively, power source 30 may be part of handle 34 or base 36, and may be activated or deactivated by the switch or button.

In use, with the subject resting on the top surface of operating table 16, the user may insert shaft 32 into the subject. The insertion step may include the user using one hand to guide shaft 32 into the subject. Additionally or alternatively, the insertion step may include the user moving base 36 distally, with handle 34 supported on base 36, to insert shaft 32. The user may continue to move shaft 32 distally until the distal end of shaft 32 is in a target area inside the subject's body, such as, for example, in the subject's urethra, bladder, or ureter. Additionally, the user may continue to slide shaft 32 so its distal end moves from the ureter into the subject's kidney.

During insertion of shaft 32 and/or positioning of the distal end of shaft 32 at the target area, the user may manipulate controls on handle 34, thereby facilitating insertion by deflecting, rotating, and/or translating shaft 32. With the distal end of shaft 32 at the target area, and with the target area in view of the visualization system 38, the user may perform a procedure. For example, the user may locate a kidney stone. The user may move the distal end of shaft 32 to aim optical fiber 50 of laser energy system 20 at the kidney stone. Additionally or alternatively, the user may move optical fiber 50 towards or away from the kidney stone for aiming purposes.

The user may activate or otherwise prepare laser energy system 20 to fire laser energy. The user may then fire the laser energy toward the kidney stone from the distal end of optical fiber 50, fragmenting the kidney stone. If fragmented into small enough pieces, the fragments of the kidney stone may be flushed out of the target area with the fluid from fluid system 22. That is, the fluid from fluid system 22 may be directed through endoscope system 12 and out of the distal end of shaft 32, and into the target area. The fluid may flush out the target area, and then exit the target area via the ureter, bladder, and urethra, taking the fragments with it. Alternatively, the fluid (and fragments) may exit the target area via shaft 32. The fluid may also flush out other fluids or solid materials from the target area, keeping clear the user's view of the target area. It is also contemplated that the fluid may generate pressure against the tissue surrounding the target area, thus helping to expand the size of the passage in the ureter and/or the size of one or more cavities in the kidney. This expansion may create space to move shaft 32 and optical fiber 50, thus making it easier to locate and fragment the kidney stone. The expansion may also facilitate flushing of the target area by providing more room for fluid flow. The fluid may include, for example, saline, or any other suitable fluid.

In some instances, one or more of the fragments may be large enough that further fragmentation may be desired. In such an instance, the user may move shaft 32 and/or optical fiber 50 to aim the distal end of optical fiber 50 at the fragment. The user may then break the fragment apart into smaller fragments using the above-described steps. This process may be repeated until the fragments are small enough to be flushed out of the target area by the fluid. Additionally or alternatively, retrieval basket system 52 may be inserted into endoscope system 12 and out the distal end of shaft 32 into the target area, to grasp and remove the fragments. Additionally or alternatively, a thermosensitive polymer gel may be injected into the target area via the distal end of shaft 32 to capture and/or bind fragments. The thermosensitive polymer gel, when injected, may become increasingly viscous as it absorbs heat from its surroundings, trapping fragments therein. The thermosensitive polymer gel and fragments trapped therein may be removed from the target area. Additionally or alternatively, the stone fragments and/or thermosensitive polymer gel may be suctioned out of the subject via a vacuum system (not shown) in fluid communication with the distal end of shaft 32.

While a laser lithotripsy procedure taking place in the subject's urinary tract has been described, it should be understood that a different procedure may be performed in a similar or different target area of the subject's body. For example, the target area may include any of the other organs of the subject, and the procedure may include any other treatment procedure including, for example, using energy (e.g., thermal) to cut, ablate, and/or coagulate tissue in the target area.

An endoscope system 100, shown in FIGS. 3A-3D, is one example of endoscope system 12 of FIG. 2. Endoscope system 100 may include a shaft 102, a handle 104, and a base 106. Shaft 102, handle 104, and base 106 may correspond to shaft 32, handle 34, and base 36 of FIG. 2. The proximal end of shaft 102 may be coupled to a lower end of handle 104, at a distal facing side of handle 104. Shaft 102 may be joined to handle 104 by a movable coupling 108. Movable coupling 108 may form part a shaft control system 109 corresponding to shaft control system 46 of FIG. 2. Movable coupling 108 may allow shaft 102 to move relative to handle 104 in proximal and distal directions. In one example, movable coupling 108 may include a telescoping connection, such that shaft 102 may slide proximally and distally relative to handle 104. In another example, movable coupling 108 may include a threaded connection, such that shaft 102 may move proximally and distally relative to handle 104 when shaft 102 is rotated about its central longitudinal axis. In yet another example, movable coupling 108 may include a knob or wheel (not shown) engaging the exterior surface of shaft 102, such that rotation of the knob or wheel may cause translation of shaft 102. With handle 104 gripped in one hand, the user may use his or her other hand to manipulate movable coupling 108. In yet another example, movable coupling 108 may include an electronic actuator (not shown), such as a motor, configured to impart translation to shaft 102 when the electronic actuator is activated. Movable coupling 108 may provide the user with the ability to make adjustments to the position of the distal end of shaft 102 after the distal end of shaft 102 has already been initially positioned in the target area, the adjustments being finer than those made during inserting of shaft 102 into the subject.

Handle 104 may include a housing 110 configured for gripping by the user. For example, housing 110 may have an exterior surface shaped and/or textured to facilitate gripping by the user in, for example, one of the user's hands. With the user gripping housing 110, such that the user's palm contacts the exterior surface of housing 110, the user's thumb may be capable of reaching an upper end of housing 110. A lever 112 may be movably coupled to housing 110 proximate the upper end. For example, lever 112 may be coupled to a side of housing 110, near the upper end of housing 110, by a pivot 114. Lever 112 may rotate about pivot 114, thereby moving in proximal and distal directions. Lever 112 may form another part of shaft control system 109. Lever 112 may be operatively couple to proximal ends of the steering cable(s) (not shown). The steering cable(s) may extend into shaft 102, with distal ends of the steering cable(s) being operatively coupled to the distal end of shaft 102. Movement of lever 112 may push and/or pull the steering wire(s) to tilt, bend, or otherwise deflect the distal end of shaft 102 in, for example, an up-down motion and/or a left-right motion. The user may move lever 112 proximally and distally using his or her thumb.

The lower end of handle 104 may include ports 116 and 118. Each of ports 116 and 118 may be in communication with one or more lumens (not shown) in shaft 102. Port 116 may receive fluid from fluid system 22. Port 118 may receive one or more instruments, such as optical fiber 50 of laser energy system 20, and/or retrieval basket system 52. Ports 116 and 118 may be on opposing sides of handle 104. Though a port 116 for fluid and a port 118 for instruments is depicted, handle 104 may include a single port or more than two ports. For example, additional ports may be provided for receiving additional instruments, so those instruments may be used simultaneously, rather than just interchangeably in a single port. It should be understood that the location of port 116 and/or port 118 on handle 104 may be moved depending on the requirements of the user.

Handle 104 may include an instrument control system 120 (corresponding to instrument control system 48 in FIG. 2). Instrument control system 120 may include one or more buttons or a switch 122, such as a rocker switch, that may be operatively coupled to an actuator (not shown) (corresponding to actuator(s) 58 in FIG. 2). The actuator may include, for example, an electric motor contained within housing 110. The actuator may engage the exterior surface of optical fiber 50, retrieval basket system 52, and/or any other instrument inserted into port 118. When a first side of switch 122 is depressed by the user, the actuator may be activated to drive the instrument in the distal direction. When a second side of switch 122 is depressed, the actuator may be activated to drive the instrument in the proximal direction. It is contemplated that switch 122, when depressed, may continue to move the instrument until switch 122 is allowed to return to a rest position. Alternatively, the instrument may move a predetermined distance when switch 122 is depressed. Further incremental movements of the instrument may be carried out by keeping switch 122 depressed, or by allowing switch 122 to return to its rest position, and then depressing switch 122 again. Alternatively, depressing switch 122 halfway may cause the instrument to move in predetermined increments of distance, and depressing switch 122 fully may cause the instrument to move continuously as long as switch 122 remains fully depressed. Such features may assist with fine adjustment of the position of the distal end of the instrument.

When switch 122 is at rest, the actuator may lock the instrument in place. Alternatively, when switch 122 is at rest, the actuator may be disengaged from the instrument, allowing the user to move the instrument proximally and distally manually. In yet another alternative, switch 122 may be omitted. The actuator may instead include a knob or wheel (not shown) that engages the exterior surface of the instrument via any suitable system known in the art. The user may manually rotate the knob/wheel to drive the instrument in the proximal and distal directions. Control over the proximal/distal movement of the instrument may help the user aim or position the distal end of the instrument with greater precision than would otherwise be the case.

Handle 104 may include a laser control system 124 corresponding to laser control system 20 of FIG. 2. Laser control system 124 may include a laser firing control system 126 used to fire laser energy from laser energy system 20 at a suitable target. Laser firing control system 126 may include a switch or button 128 at the proximal end of housing 110 of handle 104. For example, button 128 may be positioned on a side of housing 110 such that button 128 may be depressed by the user's pointer finger when handle 104 is against the palm of the user's hand. Depressing button 128 may cause laser energy system 20 to fire laser energy. It is contemplated that the laser energy may be fired in different modes. For example, in one mode of operation, the laser energy may continue to fire in bursts of predetermined duration or in a continuous stream as long as button 128 remains depressed. This may allow the user to deliver a large amount of laser energy in a short period of time. Additionally or alternatively, in another mode, the laser energy may fire in a single burst of predetermined duration regardless of whether or not button 128 remains depressed. This may help safeguard against accidentally discharging the laser energy at an unintended target due to unexpected movement of endoscope system 100 or the subject that may throw off the user's aim. Additionally or alternatively, fully depressing button 128 may fire a continuous stream of the laser energy, while depressing button 128 halfway may fire one or more bursts of predetermined duration. Additionally or alternatively, in another mode of operation, laser energy system 20 may not fire a subsequent burst or stream of laser energy for a predetermined period of time after an initial firing. This may ensure that there is sufficient time for heat to be dissipated from the target area, thus protecting tissue from heat damage, before any additional firing of the laser energy. Button 128 and lever 112 may be actuated by a single hand of the user (using, e.g., the pointer finger and thumb of the single hand) while the single hand grips handle 104. It is contemplated that button 128 and lever 112 may be actuated simultaneously, for example, to control positioning of the distal end of shaft 102 when firing the laser energy.

Laser control system 124 may include a button 130 for controlling laser sweeping. Button 130 may, for example, activate an electric motor or other actuator operatively coupled to proximal ends of the steering cable(s) (not shown) of shaft 102. The pressing of button 130 may activate the actuator to push and/or pull the steering wire(s) to tilt, bend, or otherwise deflect the distal end of shaft 102 in, for example, an up-down motion and/or a left-right motion, thereby causing a similar deflection (e.g., sweeping) of optical fiber 50 when it is in shaft 102. The user may press button 130 using his or her thumb. Additionally or alternatively, button 130 may bring a pivoting element (not shown), pivotably coupled at the distal end of shaft 102, into engagement with the distal end of optical fiber 50, to cause the distal end of optical fiber 50 to deflect.

Handle 104 may be removably coupled to base 106. Handle 104 may be received by a dock 132 of base 106. Dock 132 may include, for example, a protrusion 134 configured to mate with a complementary recess (not shown) on the lower surface of handle 104. Protrusion 134 and the recess may form a snap-fit connection that engages to secure handle 104 to dock 132 when handle 104 is pressed onto dock 132 with a sufficient downward force. Handle 104 may remain secured to dock 132 until a sufficient upward force is exerted on handle 104 to break the snap-fit connection.

Figure 3A:
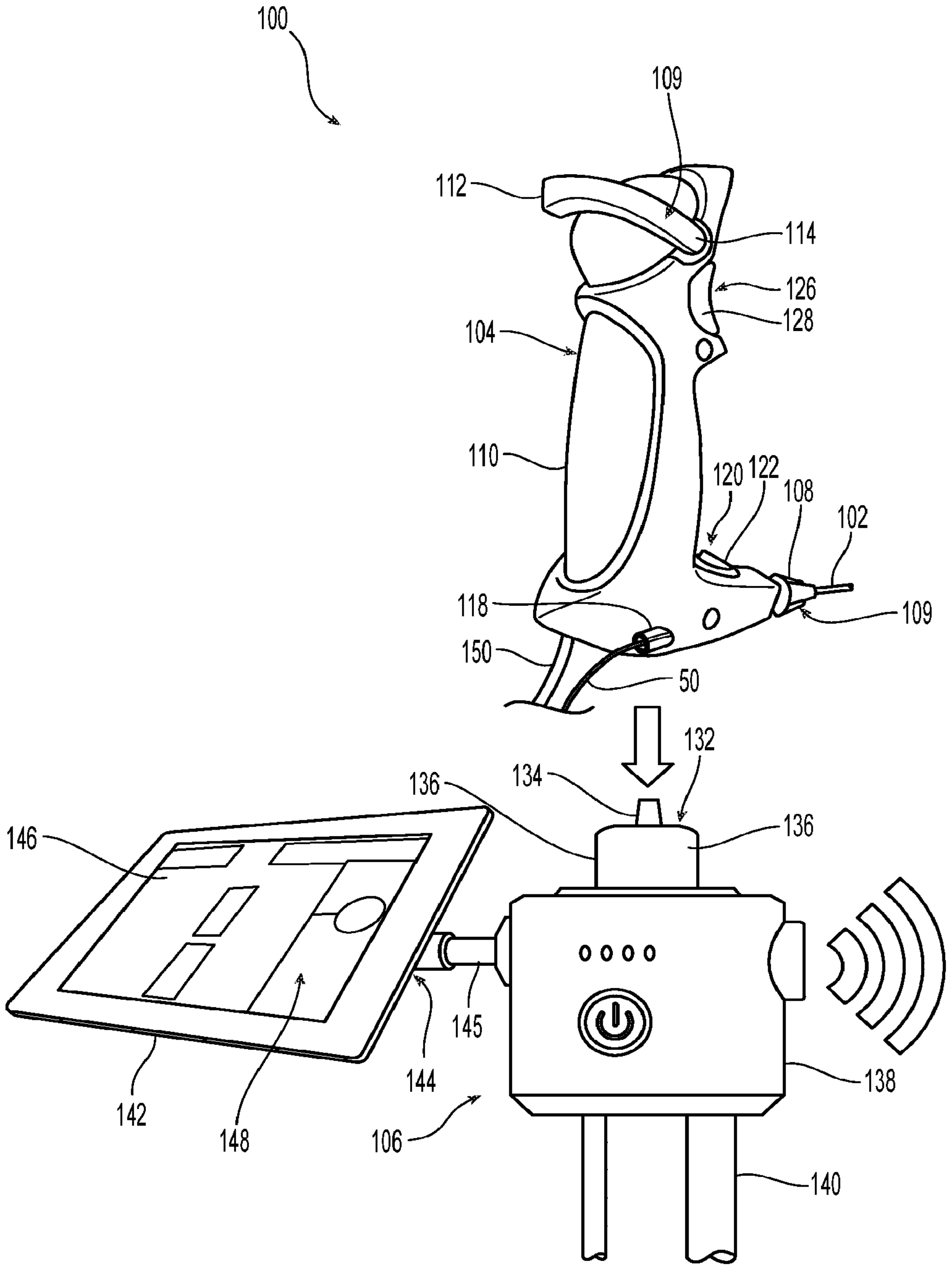
FIG. 3A is a perspective view of a handle, shaft, and base of an endoscope system, in accordance with aspects of the present disclosure.
Figure 3B:
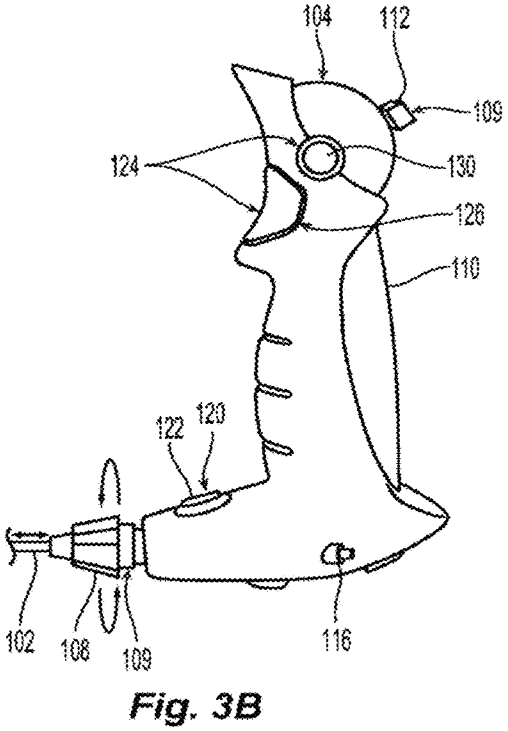
FIG. 3B is another perspective view of the handle and shaft of FIG. 3A, in accordance with aspects of the present disclosure.
Figure 3D:
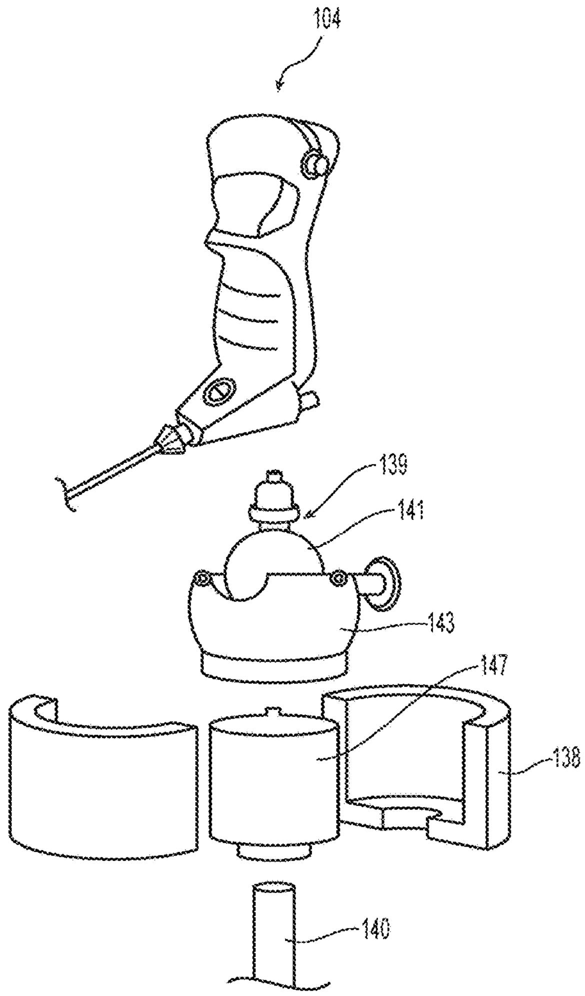
FIG. 3D shows an exploded view of the handle and base of FIG. 3A, in accordance with aspects of the present disclosure.
Figure 3C:
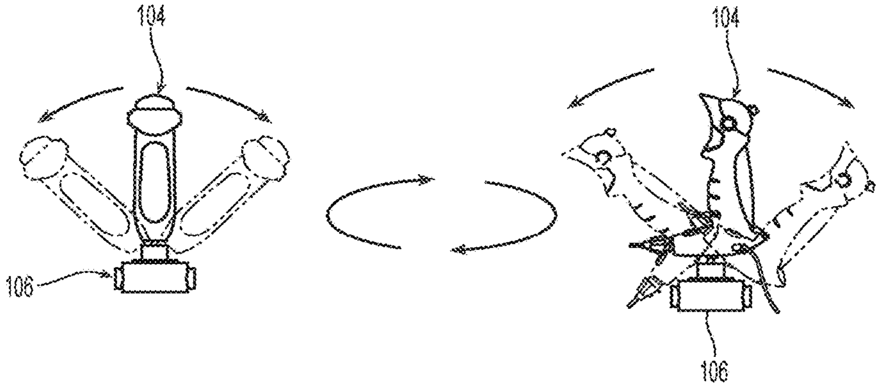
FIG. 3C shows front and side views of the handle, shaft, and base of FIG. 3A, in accordance with aspects of the present disclosure.

Dock 132 may include a stem 136 extending between protrusion 134 and a housing 138 of dock 132. Stem 136 and housing 138 may be movably coupled. For example, stem 136 may include a ball 141 and housing 138 may include a complementary socket 143 therein, forming a ball and socket joint/connection 139 (FIG. 3D), allowing multidirectional movement and rotation of stem 136 relative to housing 138. Exemplary movements are depicted in FIG. 3C. Lateral pivoting of handle 104 (shown to the left in FIG. 3C), twisting of handle 104 (shown in the middle in FIG. 3C), and/or proximal and distal pivoting of handle 104 (shown to the right in FIG. 3C) may be performed, to effect movement/positioning of shaft 102.

Ball and socket connection 139 may be configured (e.g., sized) to frictionally engage, such that ball 141 will not move relative to socket 143 unless the user exerts a sufficient force to overcome the frictional engagement. Thus, the position/orientation of handle 104 may be maintained, even after the user removes his or her hand from handle 104, by the frictional engagement.

Additionally or alternatively, housing 138 may include, or may contain within it, one or more gyroscopic mounts/actuators 147 that may engage stem 136. The gyroscopic mount(s) 147 may form part of actuator(s) 63 in FIG. 2. The gyroscopic mount(s) 147 may maintain handle 104 in a fixed position/orientation if the user removes his or her grip from handle 104. It is contemplated that housing 138 may include three gyroscopic mounts 147, with one gyroscopic mount each for maintaining the lateral position/orientation, proximal and distal position/orientation, and rotational position/orientation of handle 104 after the user removes his or her grip. This may provide the user with the freedom to use his or her gripping hand to perform other tasks without resulting in a loss of the desired positioning of handle 104 and shaft 102. It is also contemplated that the electronic components in housing 138 may be activated and deactivated by actuating an on/off button (FIG. 3A) on housing 138.

Housing 138 may be coupled to a support member 140. Support member 140 may support housing 138 on the ground or on operating table 16. Support member 140 may be slidable on the ground or on operating table 16, to move endoscope system 100 toward/away from the subject, thereby facilitating insertion/withdrawal of shaft 102 into/out of the subject's body.

Base 106 may include a tablet computer 142, or any other suitable computing device. Tablet computer 142 may correspond to control unit(s) 18 of FIG. 2. Tablet computer 142 may be coupled to housing 138 by a supporting device 144. Supporting device 144 may include an arm 145, and arm 145 may be adjustable to help position tablet computer 142 for easy viewing and/or manipulating by the user.

Tablet computer 142 may include a display system 146, which may correspond to display system 62 of FIG. 2. Display system 146 may provide a touch-screen user interface 148 that the user may utilize to monitor the subject and/or the endoscopy system 10, and/or to control aspects of the endoscopy system 10. For example, it is contemplated that tablet computer 142 may be operatively coupled to auxiliary system(s) 14 via wired or wireless connections. In one example, tablet computer 142 may be coupled to power source 30 via cables/wires (not shown) that connect tablet computer 142 to housing 138 through or along arm 145. Handle 104 may be coupled to power source 30 via a connector 150, which may include one or more cables/wires, that connects handle 104 to housing 138. A cable/wire (not shown) may connect housing 138 to power source 30.

Additionally or alternatively, laser control system 124 may be operatively coupled to housing 138 via the cables/wires in connector 150. Housing 138 may be operatively coupled to tablet computer 142 via cables/wires running through or along arm 145, or alternatively, housing 138 may communicate wirelessly with tablet computer 142. Housing 138 and/or tablet computer 142 may communicate wirelessly with laser energy system 20. As such, pressing button 128 may send instructions to laser energy system 20, via housing 138 and/or tablet computer 142, to fire laser energy.

Additionally or alternatively, operational parameters/settings of laser energy system 20, fluid system 22, illumination system 40, and/or monitored vitals of the subject, may be communicated to tablet computer 142, directly or via housing 138, for display on display system 146. It is contemplated that the user may manipulate user interface 148 to provide instructions for setting/modifying the operational parameters/settings of laser energy system 20 and/or fluid system 22, and those instructions may be communicated to housing 138, laser energy system 20, and/or fluid system 22. It is also contemplated that image data from visualization system 38 may be communicated to tablet computer 142 for display on display system 146 in addition to, or alternatively to, display system 28, so that the user may view the target area while gripping handle 104.

Figure 4A:
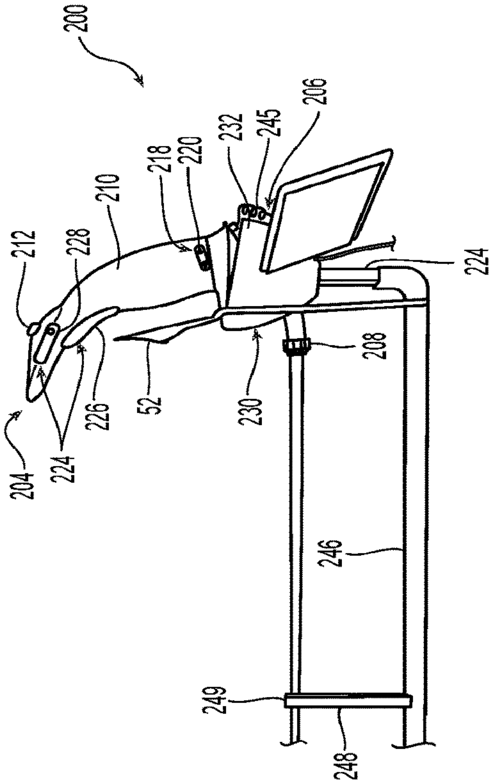
FIG. 4A is a perspective view of part of a handle, shaft, and base of an endoscope system, in accordance with aspects of the present disclosure.
Figure 4C:
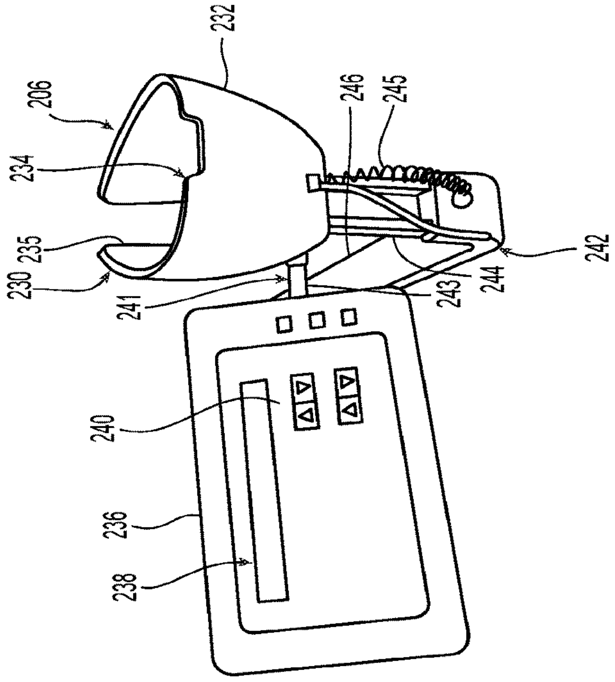
FIG. 4C is a perspective view of the base of FIG. 4A, in accordance with aspects of the present disclosure.
Figure 4B:
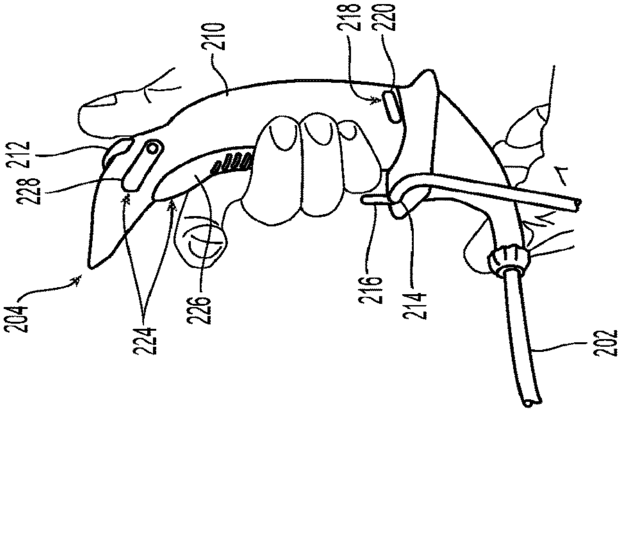
FIG. 4B is a perspective view of the handle and shaft of FIG. 4A, in accordance with aspects of the present disclosure.
Figure 5A:
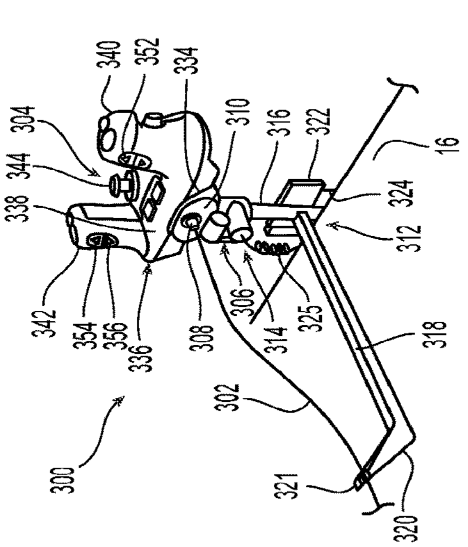
FIG. 5A is a perspective view of a handle, shaft, and base of an endoscope system, adjacent an operating table, in accordance with aspects of the present disclosure.
Figure 5B:
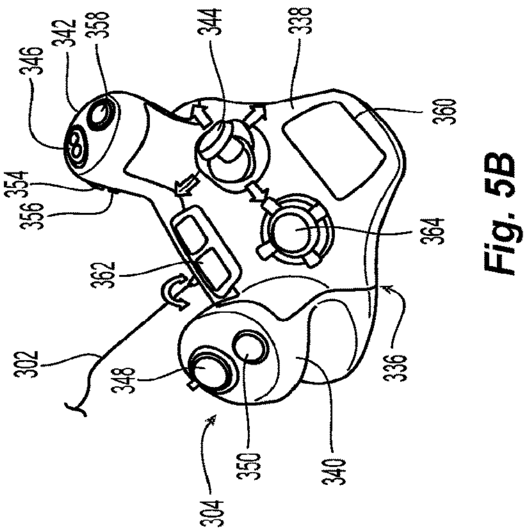
FIG. 5B is another perspective view of the handle of FIG. 5A, in accordance with aspects of the present disclosure.
Figure 5C:
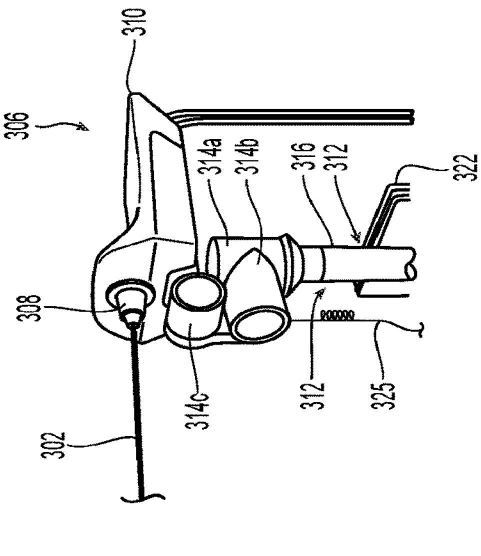
FIG. 5C is another perspective view of the base and shaft of FIG. 5A, in accordance with aspects of the present disclosure.
Figure 5D:
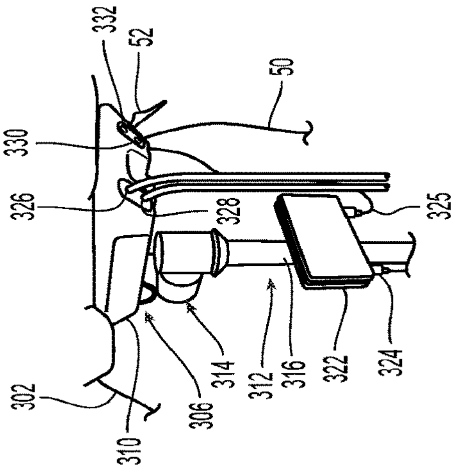
FIG. 5D is another perspective view of the base of FIG. 5A, in accordance with aspects of the present disclosure.

An endoscope system 200, shown in FIGS. 4A-4C, is another example of endoscope system 12 of FIG. 2. Endoscope system 200 may include a shaft 202, a handle 204, and a base 206 corresponding to shaft 32, handle 34, and base 36 of FIG. 2. In FIGS. 4A-4C, the proximal end of shaft 202 may be coupled to a lower end of handle 204, at a distal facing side of handle 204. Shaft 202 may be joined to handle 204 by a movable coupling 208 (similar to movable coupling 108 of FIGS. 3A-3D). Similar parts of endoscope systems 100 and 200 may have similar constructions and/or may operate in a similar manner, unless described otherwise.

Handle 204 may include a housing 210 configured for gripping by the user. For example, housing 210 may have an exterior surface shaped and/or textured to facilitate gripping by the user in, for example, one of the user's hands. With the user gripping housing 210, such that the user's palm contacts the exterior surface of housing 210, the user's thumb may be capable of reaching an upper end of housing 210. A pivoting lever 212 (similar to lever 112 of FIGS. 3A-3D) may be movably coupled to housing 210.

Handle 204 may include ports 214 and 216 (similar to ports 116 and 118 of FIGS. 3A-3D). Each of ports 214 and 216 may be in communication with one or more lumens (not shown) in shaft 202. Port 214 may receive fluid from fluid system 22. Port 216 may receive one or more instruments, such as optical fiber 50 of laser energy system 20, and/or retrieval basket system 52. It should be understood that handle 204 may include fewer or more ports, depending on the requirements of the user. It should also be understood that the location of port 214 and/or port 216 may be moved. Moreover, port 116 and/or port 118 may be moved near instrument control system 120 of handle 104, similar to the positioning of ports 214 and 216.

Handle 204 may include an instrument control system 218, including a switch 220 that may be operatively coupled to an actuator 222; and a laser control system 224 including a laser firing button 226, and/or a laser sweeping button 228 (each of which may be similar to corresponding components in FIGS. 2 and 3A-3D). Lever 212, laser firing button 226, and laser sweeping button 228 may be actuated by a single hand of the user (using, e.g., the pointer finger and thumb of the single hand) while the single hand is gripping handle 204.

Handle 204 may be removably coupled to base 206. Handle 204 may be received by a dock 230 of base 206. Dock 230 may include, for example, a cup, cradle, or housing 232 on base 206. Housing 232 defines a central recess 234 for receiving the lower end of handle 204, and a slot 235 for receiving the end of handle 204 that is coupled to shaft 202. The user may slide handle 204 down into and up out of housing 232 while the user is gripping handle 204. When handle 204 is within housing 232, movable coupling 208 may protrude distally out of slot 235, making movable coupling 208 accessible to the user even when handle 204 is docked. Handle 204 and dock 230 may be sized such that handle 204 may undergo multidirectional movement and rotation relative to dock 230 while sitting within dock 230 (including, for example, movements/rotations shown in FIG. 3C). Dock 230 may remain stationary relative to handle 204. Alternatively, housing 232 may be made of a flexible and/or elastic material, such that housing 232 may deform as the user's manipulation of handle 204 forces handle 204 against housing 232. Housing 232 may return to its rest/undeformed state (FIG. 4C) in the absence of such force(s).

Base 206 may include a tablet computer 236 (similar to tablet computer 142) with a display system 238 and user interface 240, or any other suitable computing device. Tablet computer 236 may be coupled to housing 232 by a supporting device 241, such as an arm 243, each of which may be similar to corresponding components shown in FIGS. 3A-3D. Tablet computer 236 and/or handle 204 may be operatively coupled to power source 30, auxiliary system(s) 14, visualization system 38, and/or illumination system 40, via one or more connectors 245 (similar to connector 150, and/or cables/wires, of FIGS. 3A and 3C).

Base 206 may include a support member 242 for supporting dock 230 and shaft 202 on, for example, operating table 16. Support member 242 may include a proximal vertical leg 244, positioned at its proximal end. Proximal vertical leg 244 may be height adjustable for setting/adjusting a height of dock 230 and handle 204. Support member 242 may also include a horizontal leg 246 extending distally from vertical leg 244. Support member 242 may also include a distal vertical leg 248. Distal vertical leg 248 may extend upwards from horizontal leg 246. Distal vertical leg 248 may include a slot 249 for receiving shaft 202. Shaft 202 may slide within slot 249. In one example, the outer diameter of shaft 202 may be greater than a width of slot 249, such that slot 249 may exert a holding force on shaft 202 when shaft 202 is inserted therein. Distal vertical leg 248 may make it easier to control shaft 202 at least because the user may not have to support the full weight of shaft 202, or even a partial weight of shaft 202, thus reducing user fatigue.

Moreover, in conventional endoscope systems, a user may hold the endoscope handle and the endoscope shaft manually during performance of a procedure. Typically the thumb and forefinger of the user's non-dominant hand may be positioned on the endoscope shaft to maintain its position, to prevent retropulsion on advancement of instruments (e.g., wires, baskets, and/or other tools) distally through one or more lumens of the endoscope shaft. Distal vertical leg 248 may allow the user to keep one of his or her hands free from shaft 202, thereby reducing the overall cognitive load acting on the user, and freeing the user's non-dominant hand for performing other tasks. Additionally or alternatively, the user may also be able to lock the length of shaft 202 once it is inserted into the subject's body via engagement of shaft 202 with slot 249 of distal vertical leg 248. This may prevent any unwanted proximal and/or distal movements of shaft 202 during the procedure. Maintenance of shaft 202 in position in the subject's body may help the user maintain a desired field of view inside the subject's body. One or more of these may make endoscope system 200 more ergonomic to the user, and may enhance the user's procedural efficiency.

An endoscope system 300, shown in FIGS. 5A-5D, is another example of endoscope system 12 of FIG. 2. Endoscope system 300 may include a shaft 302, a handle 304, and a base 306 corresponding to shaft 32, handle 34, and base 36 of FIG. 2. The proximal end of shaft 302, however, may be coupled to base 306, instead of to handle 304. Shaft 302 may be joined to base 306 by a movable coupling 308 (similar to movable coupling 108 of FIGS. 3A-3D). Similar parts of endoscope systems 100, 200, and 300 may have similar constructions and/or may operate in a similar manner, unless described otherwise Base 306 may include a dock 310. Dock 310 may be movably coupled to a support member 312. Support member 312 may support dock 310 on operating table 16 and/or the floor. The movable coupling may be provided by, for example, one or more joints or hinges 314. Joint(s)/hinge(s) 314 may include three pivoting members 314*a*, 314*b*, and 314*c*, having perpendicular pivot axes. By adjusting joint(s)/hinge(s) 314, the orientation of dock 310 may be adjusted in planes defined by one or more of the pivot axes (e.g., being capable of roll, pitch, and yaw movements). Additionally or alternatively, joint(s)/hinge(s) 314 may include gyroscopic mount(s) (corresponding to actuator(s) of FIG. 2, and similar to gyroscopic mount(s) 147 of FIG. 3D) that may allow pivoting about one or more of the pivot axes when force(s) are exerted on dock 310 by the user (e.g., via handle 304), and may maintain dock 310 in a fixed position/orientation in the absence of the force(s).

Support member 312 may be similar to support member 242 of FIGS. 4A-4C. Support member 312 may be slidable on the ground or on operating table 16 to move endoscope system 300 toward/away from the subject, thereby facilitating insertion/withdrawal of shaft 302 into/out of the subject's body. Support member 312 may include a proximal vertical leg 316 at its proximal end. Proximal vertical leg 316 may be height adjustable to set/adjust a height of dock 310 and handle 304. Support member 312 may also include a horizontal leg 318 extending distally from proximal vertical leg 316. Support member 312 may also include a distal vertical leg 320. Distal vertical leg 320 may extend upwards from horizontal leg 318. Distal vertical leg 320 may include a slot 321 for receiving shaft 302. Shaft 302 may slide within slot 321.

A control unit 322 (corresponding to control unit(s) 18 of FIG. 2) may be coupled to base 306. Control unit 322 may be coupled to power source 30 via cables/wires 324. Dock 310 may be operatively coupled to control unit 322 via a connector 325. Additionally or alternatively, a tablet computer (not shown) similar to tablet computers 142 and 236 may be used in place of control unit 322, or to supplement control unit 322.

The proximal end of dock 310 may include ports 326, 328, 330, and 332. Each of ports 326, 328, 330, and 332 may be in communication with one or more lumens (not shown) in shaft 302. Port 326 may receive fluid from fluid system 22 for delivery to the target area via dock 310 and shaft 302. Port 328 may return fluid to fluid system 22 from the target area via shaft 302 and dock 310. Ports 330 and 332 may receive instruments, such as optical fiber 50 of laser energy system 20 and retrieval basket system 52. Though multiple ports 326, 328, 330, and 332 are depicted, it is contemplated that dock 310 may include fewer ports or more than four ports.

Handle 304 may be removably coupled to base 306. For example, a lower surface of handle 304 may include a recess 334 for receiving dock 310, with dock 310 having a shape complementary to that of recess 334 to provide close contact between dock 310 and handle 304. Handle 304 may be operatively coupled to dock 310 by a connector (not shown), with the connector directing power from dock 310 to handle 304 and/or providing a communications link for signals to be sent between electronic components of handle 304 and dock 310. Alternatively, handle 304 may receive power wirelessly from dock 310 via inductive charging, and/or handle 304 may communicate with dock 310 via wireless communication.

Handle 304 may include a housing 336 configured for gripping by the user. Housing 336 may have a horizontal portion 338, and two vertical portions 340 and 342 extending upward therefrom, to facilitate gripping by the user with both hands. The user may wrap his or her palms and fingers around vertical portions 340 and 342, with the blades of the user's hands facing and/or contacting opposing side regions of horizontal portion 338, and the user's thumbs positioned in range of reaching the upper ends of vertical portions 340 and 342 and/or the central region of horizontal portion 338.

Handle 304 may include, for example, a joystick 344 and/or buttons or a switch 346 (e.g., a rocker switch), corresponding to shaft control system 46 of FIG. 2. Joystick 344 may pivot, rotate, or otherwise articulate in one or more directions relative to housing 336, and/or sides of switch 346 may be depressed, with such movements resulting in movement(s) of shaft 302. For example, a monitoring device (not shown) in handle 304 may monitor movement of joystick 344 and/or switch 346, and may send one or more output signals based on the movement. One or more actuators (not shown) (corresponding to actuator(s) 63 in FIG. 2) in dock 310, in the form of electric motors, may receive the output signals. The actuator(s) may be operatively coupled to one or more steering cables in shaft 302, and/or to movable coupling 308, such that the actuator(s) may push and/or pull the steering cables to deflect shaft 302 (left-right and/or up-down), rotate shaft 302 about its central longitudinal axis, and/or translate shaft 302 proximally and distally, based on the output signals.

Handle 304 may include a knob 348 (corresponding to visualization control system 42 of FIG. 2), rotatable in clockwise and/or counterclockwise directions for controlling zoom, focus, and/or any other operational parameters of visualization system 38. Handle 304 may further include a button 350 (corresponding to illumination control system 44 of FIG. 2) for controlling activation/deactivation, intensity, and/or any other operational parameters of illumination system 44. Knob 348 and/or button 350 may be located on the upper end of vertical portion 340, in range of the user's left thumb.

Handle 304 may include buttons or a switch 352 (corresponding to instrument control system 48 of FIG. 2) for moving an instrument (e.g., optical fiber 50 or retrieval basket system 52) distally and proximally so as to extend and retract the instrument relative to the distal end of shaft 302. Switch 352 may include a rocker switch. When the user presses a first side of switch 352, an actuator (not shown) (corresponding to actuator(s) 63 in FIG. 2) may move the instrument distally, and when the user presses a second side of switch 352, the actuator may move the instrument proximally. Switch 352 may positioned on a side surface of vertical portion 340, in range of the user's pointer finger when the user is gripping vertical portion 340 with his or her left hand.

Handle 304 may include buttons 354, 356, and 358 (corresponding to laser control system 54 of FIG. 2). For example, button 356 may trigger or otherwise control firing of the laser energy from laser energy system 20. Button 354 may signal laser energy system 20 prior to firing the laser energy, to prepare laser energy system 20 for firing. Buttons 354 and 356 may be positioned on a side surface of vertical portion 342, in range of the user's pointer finger when the user is gripping vertical portion 342 with his or her right hand. Button 358 may control laser sweeping, and may be positioned on the upper surface of vertical portion 342, in range of the user's thumb when the user is gripping vertical portion 342 with his or her right hand.

The user may manipulate the controls on the right side of handle 304 (e.g., elements 344, 354, 356, and 358) with his or her right hand, while the right hand grips vertical portion 342. The user may manipulate the controls (e.g., elements 354 and 356) on the proximal-facing lateral surface of vertical portion 342 with his or her right pointer finger. The user may manipulate the controls (e.g., elements 346 and 358) on the upper surface of vertical portion 342, and the control (e.g., element 344) on the upper surface of horizontal portion 338, with his or her right thumb. The user may manipulate the controls with his or her right finger and right thumb simultaneously, or one at a time.

The user may manipulate the controls on the left side of handle 304 (e.g., elements 348, 350, 352, 362, and 364) with his or her left hand while the left hand grips vertical portion 340. The user may manipulate the control (e.g., element 352) on the proximal-facing lateral surface of vertical portion 340 with his or her left pointer finger. The user may manipulate the controls (e.g., elements 348 and 350) on the upper surface of vertical portion 340, and the controls (e.g., elements 362 and 364) on the upper surface of horizontal portion 338, with his or her left thumb. The user may manipulate the controls with his or her left finger and left thumb simultaneously or one at a time. Additionally or alternatively, the user may manipulate the controls on the left side of handle 304 and the right side of handle 304 simultaneously or one at a time.

Handle 304 may include a display system 360. Display system 360 may include a screen, monitor, array of lights, and/or any other suitable display mechanism. Display system 360 may show, for example, auxiliary systems settings, information on the subject, operational parameters associated with endoscope system 300, and/or any other suitable data. Display system 360 may be positioned at a proximal end of the upper surface of horizontal portion 338. Alternatively, display system 360 may be omitted from handle 304.

Handle 304 may also include a button 362 and a joystick 364. Button 362 may be used to access handle settings including, for example, the brightness of display system 360 and/or any other operational parameters of handle 304. Those settings may be displayed on display system 360. Joystick 364 may be used to navigate/select/adjust those settings. Additionally or alternatively, joystick 364 may access settings of auxiliary system(s) 14, such as fluid system 22 and/or laser energy system 20, causing the settings to be displayed on display system 360. Joystick 364 may also be used to navigate/select/adjust those settings.

Figure 6:
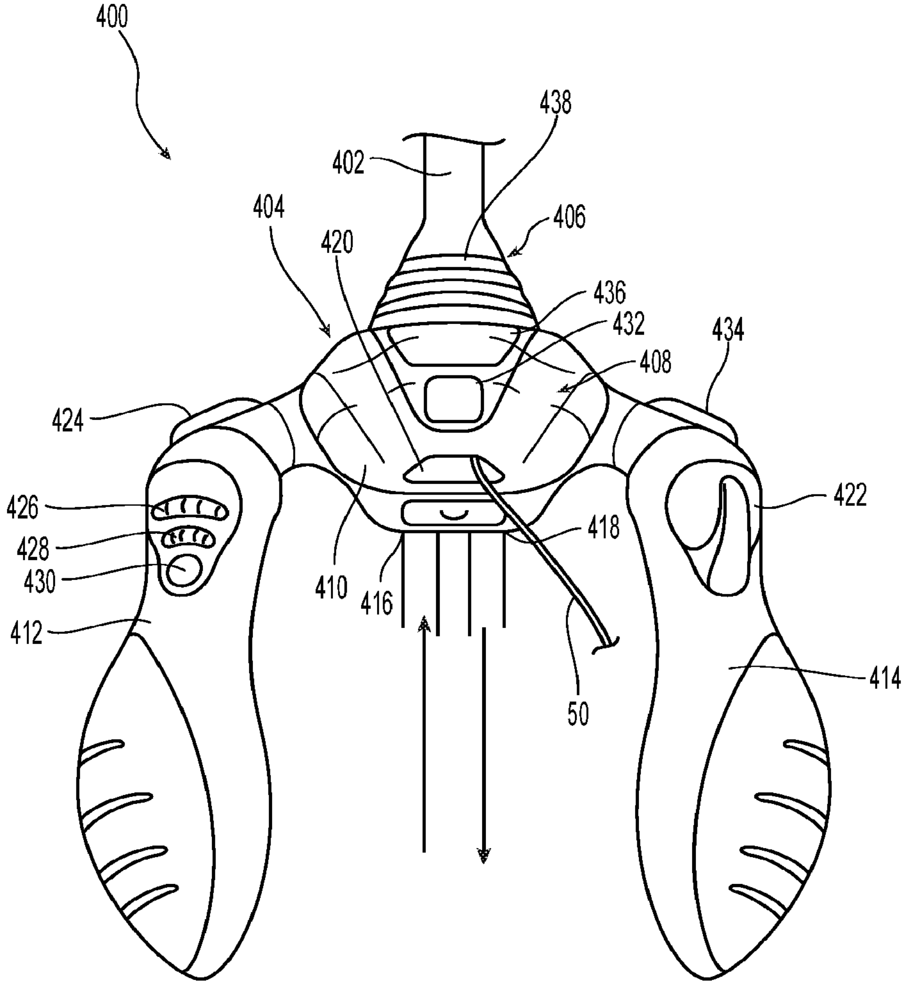
FIG. 6 is a perspective view of a handle and a shaft of an endoscope system, in accordance with aspects of the present disclosure.

An endoscope system 400, shown in FIG. 6, is another example of endoscope system 12 of FIG. 2. Endoscope system 400 may include a shaft 402 and a handle 404, corresponding to shaft 32 and handle 34 of FIG. 2, respectively. However, endoscope system 400 is depicted without a base. While endoscope system 400 may be used without a base, it should be understood that this is not a requirement. That is, endoscope system 400 may also be used with any of the bases described herein.

The proximal end of shaft 402 may be coupled to the distal end of handle 404. Shaft 402 may be joined to handle 404 by a movable coupling 406 (corresponding to movable coupling 108 of FIGS. 3A-3D). Similar parts of endoscope systems 100, 200, 300, and 400 may have similar constructions and/or may operate in a similar manner, unless described otherwise. Handle 404 may include a housing 408 configured for gripping by the user. For example, housing 408 may have an exterior surface shaped and/or textured to facilitate gripping by the user. Housing 408 may include a central body 410. A first arm 412 may extend in cantilevered fashion from a first end of central body 410. First arm 412 may be gripped by the user's left hand. A second arm 414 may extend in cantilevered fashion from a second end of central body 410. Second arm 414 may be gripped by the user's right hand. With the user gripping the exterior surfaces of first arm 412 and second arm 414, the user's thumbs may be capable of reaching one or more controls proximate the fixed ends of first arm 412 and second arm 414, the user's thumbs may be in range of one or more controls on central body 410, and/or the user's pointer fingers may be capable of reaching one or more controls on distal end surfaces of first arm 412 and second arm 414.

Central body 410 may include ports 416, 418, and 420. Each of ports 416, 418, and 420 may be in communication with one or more lumens (not shown) in shaft 402. Port 416 may receive fluid from fluid system 22, with the fluid flowing downstream through handle 404 into shaft 402, and out of shaft 402 into the target area. Port 418 may receive fluid from the target area, with the fluid flowing upstream through shaft 402 and into handle 404, and out of handle 404. Port 420 may receive one or more instruments, such as optical fiber 50 of laser energy system 20, and/or retrieval basket system 52. It is contemplated, however, that handle 404 may include fewer or more ports, depending on the needs of the user.

Handle 404 may include, for example, a knob 422 and/or a button 424, corresponding to shaft control system 46 of FIG. 2. Knob 422 may be rotated by the user's right thumb, with rotation of knob 422 being translated into deflection of shaft 402. For example, rotation of knob 422 may cause output signals to be sent to one or more actuators (not shown) (corresponding to actuator(s) 58 in FIG. 2) in handle 404, such as electric motors operatively coupled to one or more steering cables in shaft 402. The actuator(s) may push and/or pull the steering cables to deflect shaft 402 based on the output signals. Button 424 may be pressed by the user's left pointer finger to cause output signals to be sent to the actuator(s) to cause translation of shaft 402 proximally and distally.

Handle 404 may include knobs 426 and 428 (corresponding to visualization control system 42 in FIG. 2). Knobs 426 and 428 may be rotatable in clockwise and/or counterclockwise directions for controlling zoom, focus, and/or any other operational parameters of visualization system 38. Handle 404 may further include a button 430 (corresponding to illumination control system 44 of FIG. 2) for controlling activation/deactivation, intensity, and/or any other operational parameters of illumination system 40. Knob 426, knob 428, and/or button 430 may be actuated by the user's left thumb.

Handle 404 may include a switch or button 432 (corresponding to instrument control system 48 of FIG. 2) for moving an instrument (e.g., optical fiber 50 or retrieval basket system 52) distally and proximally so as to extend and retract the instrument relative to the distal end of shaft 402. Switch 432 may include a rocker switch. When the user presses a first side of switch 432, an actuator (not shown) (corresponding to actuator(s) 58 in FIG. 2) may move the instrument distally, and when the user presses a second side of switch 432, the actuator may move the instrument proximally. Switch 432 may be positioned on an upper surface of central body 410, in range of the user's thumbs when the user is gripping (or partially gripping) first arm 412 and second arm 414.

Handle 404 may include buttons 434 and 436 (corresponding to laser control system 54 of FIG. 2). For example, button 434 may trigger or otherwise control firing of laser energy from laser energy system 20. Button 434 may be positioned on an end surface of second arm 414, in range of the user's right pointer finger when the user is gripping second arm 414 with his or her right hand. Button 436 may control laser sweeping. Button 436 may be positioned on the upper surface of central body 410, in range of the user's thumbs when the user is gripping first and second arms 412 and 414.

The user may manipulate the controls on the right side of handle 404 (e.g., elements 422 and 434) with his or her right hand, while the right hand grips second arm 414. The user may manipulate the control (e.g., element 434) on the proximal-facing lateral surface of second arm 414 with his or her right pointer finger. The user may manipulate the control (e.g., element 422) on the top surface of second arm 414 with his or her right thumb. The user may manipulate the controls with his or her right finger and right thumb simultaneously, or one at a time.

The user may manipulate the controls on the left side of handle 404 (e.g., elements 424, 436, 428, and 430) with his or her left hand while the left hand grips first arm 412. The user may manipulate the control (e.g., element 424) on the proximal-facing lateral surface of first arm 412 with his or her left pointer finger. The user may manipulate the controls (e.g., elements 426, 428, and 430) on the upper surface of first arm 312 with his or her left thumb. The user may manipulate the controls with his or her left finger and left thumb simultaneously or one at a time.

The user may manipulate the controls at the middle of handle 404 (e.g., elements 432 and 436) with either of his or her thumbs while gripping the first and second arms 412 and 414 with both hands. It is contemplated that the user may manipulate the controls on the left side of handle 404, the right side of handle 404, and the middle of handle 404 simultaneously or one at a time.

Handle 404 may include a thermosensitive polymer gel reservoir 438 at a proximal end of shaft 402 and/or a distal end of handle 404. Reservoir 438 may be in fluid communication with a lumen (not shown) in shaft 402. The thermosensitive polymer gel in reservoir 438 may be injected into the target area via the lumen. This may be achieved manually by the user squeezing reservoir 438. Alternatively, a fluid injection mechanism (not shown) in reservoir 438 may be triggered by depression of a button (not shown) on handle 404, to inject the thermosensitive polymer.

Endoscopy system 400 may communicate via wired or wireless communication means with control unit(s) similar to control unit(s) 18, and/or a tablet computer similar to tablet computers 142 and 236. As such, endoscope system 400 may be operatively coupled to auxiliary system(s) 14 and/or any other electronic components.

Figure 7:
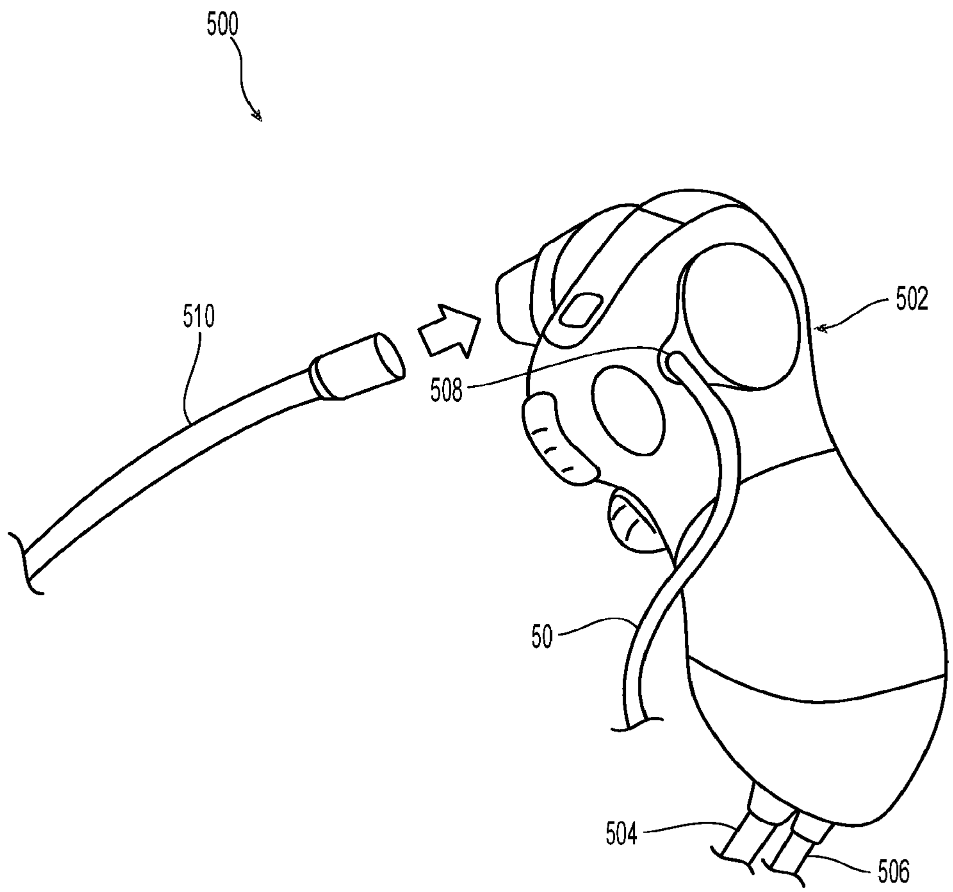
FIG. 7 is a perspective view of a handle and a shaft of an endoscope system, in accordance with aspects of the present disclosure.

An endoscope system 500, shown in FIG. 7, is an alternative version of endoscope system 500 of FIG. 6. Endoscope system 500 may include a handle 502 configured for gripping in a single hand, rather than one designed or intended for gripping with both hands. Handle 502 may include ports 504 and 506 for circulating the fluid from fluid system 22, and a port 508 for an instrument (e.g., optical fiber 50 and/or retrieval basket system 52). A proximal end of a shaft 510 may be removably attached to an upper end of handle 502. Using this type of handle may allow the user to hold handle 502 in one hand, and keep the other hand free to perform other tasks. The user may also be able to uncouple shaft 510 from handle 502, to quickly switch out one or the other. Similar parts of endoscope systems 400 and 500 may have similar constructions and/or may operate in a similar manner, unless described otherwise. Handle 502 may include one or more of the controls of handle 404. In one example, handle 502 may include all of the controls of handle 404. Additionally or alternatively, endoscopy system 500 may communicate via wired or wireless communication means with control unit(s) similar to control unit(s) 18, and/or a tablet computer similar to tablet computers 142 and 236. As such, endoscope system 500 may be operatively coupled to auxiliary system(s) 14 and/or any other electronic components.

It will be apparent to those skilled in the art that various modifications and variations can be made in the disclosed systems and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device system, comprising:

a shaft extending from a proximal end to a distal end, the shaft including a lumen extending from the proximal end to a distal opening at the distal end, wherein the lumen is configured to receive a medical instrument slidable through the lumen and through the distal opening;

a visualization system coupled to the shaft;

a handle coupled to the proximal end of the shaft and including a port in fluid communication with the lumen of the shaft, wherein the handle includes a control system configured to control operation of the shaft, the medical instrument, and/or a laser energy system;

a base including a protrusion, wherein the handle is configured to form a snap-fit connection with the protrusion; and a movable coupler joining the shaft and the handle, wherein the movable coupler is configured to translate the shaft proximally and/or distally relative to the handle;

wherein the movable coupler is distal to the handle and grippable by a first hand of a user to translate the shaft while a second hand of the user grips the handle to operate the control system.

2. The medical device system of claim 1, wherein the control system includes a lever to control bending the shaft.

3. The medical device system of claim 1, wherein the control system includes a switch operatively coupled to a motor within the handle, the switch configured to translate the medical instrument along a central longitudinal axis of the medical instrument.

4. The medical device system of claim 1, wherein the medical device system includes the laser energy system and the control system is configured to control delivery of laser energy by activating the laser energy system.

5. The medical device system of claim 1, wherein the handle is a single unitary handle of the medical device system.

6. The medical device system of claim 5, wherein the handle is configured for gripping by a single hand of a user and for activating the control system by the single hand.

7. The medical device system of claim 4, wherein the control system includes a laser firing control system.

8. The medical device system of claim 1, wherein the base includes a ball and socket connection configured for coupling with and supporting the handle, thereby allowing the handle to rotate and pivot multi-directionally relative to a remainder of the base.

9. The medical device system of claim 8, wherein the ball and socket are frictionally engaged so that a position of the handle relative to the base is maintained immediately after a user removes a hand from the handle.

10. A medical device system, comprising:

a shaft including a deflected configuration and a non-deflected configuration, wherein the shaft includes a lumen extending from a proximal opening at a proximal end of the shaft to a distal opening at a distal end of the shaft;

a visualization system coupled to the distal end of the shaft;

a handle coupled to the proximal end of the shaft, wherein the handle is configured for gripping by a hand of a user, wherein a longitudinal axis of the handle is generally perpendicular to a longitudinal axis of the shaft in the non-deflected configuration of the shaft, wherein the handle includes a control system configured to control bending of the shaft and to control a medical instrument while the medical instrument extends through the lumen of the shaft; and a movable coupler joining the shaft to the handle, wherein the movable coupler is configured to translate the shaft proximally and/or distally relative to the handle, wherein the movable coupler is distal to the handle and grippable by a first hand of a user to translate the shaft while a second hand of the user grips the handle to operate the control system.

11. The medical device system of claim 10, wherein the handle includes a plurality of buttons or switches positioned on the handle for manipulation by the second hand of the user while the second hand grips the handle, and manipulation of the plurality of buttons or switches controls bending of the shaft and/or controls the medical instrument.

12. The medical device system of claim 10, wherein the movable coupler includes a telescopic connection so that the shaft translates proximally and/or distally relative to the handle.

13. The medical device system of claim 10, wherein rotation of the movable coupler in a first direction relative to a longitudinal axis of the shaft translates the shaft proximally along the longitudinal axis, and rotation of the movable coupler in a second direction translates the shaft distally along the longitudinal axis.

14. The medical device system of claim 10, further comprising:

a base including a ball and socket connection configured for coupling with and supporting the handle; and a display configured to receive and display image data from the visualization system, wherein the handle is adjustable relative to the base by the second hand of the user while the base and the handle are coupled, and wherein the ball and socket connection is frictionally engaged so that a position of the handle relative to the base is maintained immediately after the user removes the second hand from the handle.

15. The medical device system of claim 14, wherein the base further includes a dock, wherein the dock includes a mating portion, a stem, and a housing, wherein the mating portion is configured to engage with a lower surface of the handle, wherein the stem extends between the mating portion and the housing, and wherein the stem includes the ball and the housing includes the socket complementary to the ball, forming the ball and socket connection.

16. The medical device system of claim 15, wherein the base further includes at least one gyroscopic mount coupled to the stem.

17. A medical device system, comprising:

a shaft including a proximal end and a distal end, wherein the shaft includes a lumen extending from a proximal opening of the shaft to a distal opening of the shaft, wherein the lumen is configured to receive a medical instrument therethrough;

a camera fixedly coupled to the distal end of the shaft;

a handle coupled to the proximal end of the shaft, wherein the handle includes a control system configured to control bending of the shaft, to control operation of the medical instrument extendable through the shaft, and to control a laser energy system;

a base removably coupled to the handle, thereby allowing the handle to rotate and pivot multi-directionally relative to the base, wherein the base and the handle are coupled to one another via a snap-fit connection, and wherein the base includes a ball and socket connection;

a display fixedly coupled to the base; and a movable coupler configured to translate the shaft proximally and/or distally relative to the handle.

18. The medical device system of claim 17, wherein the medical device system includes the medical instrument and the laser energy system, the medical instrument being slidable along the lumen of the shaft, wherein controlling the each of the medical instrument and the laser energy system includes manipulating buttons or switches on the handle, wherein the buttons or switches are operatively coupled to the medical instrument or the laser energy system, and wherein and the buttons are accessible to a user while the user is gripping the handle.

19. The medical device system of claim 17, wherein the movable coupler joins the shaft to the handle.

20. The medical device system of claim 17, wherein the handle and the base are frictionally engaged via the snap-fit connection so that a position of the handle relative to the base is maintained immediately after a user removes a hand from the handle.

* * * * *